United States Patent [19]

Tkatschenko et al.

[11] 4,334,435
[45] Jun. 15, 1982

[54] SEALING APPARATUS

[75] Inventors: Günter T. Tkatschenko, Muhlheim; Gunther Franke, Darmstadt, both of Fed. Rep. of Germany

[73] Assignee: The Perkin-Elmer Corporation, Norwalk, Conn.

[21] Appl. No.: 174,782

[22] Filed: Aug. 4, 1980

[30] Foreign Application Priority Data

Aug. 25, 1979 [DE] Fed. Rep. of Germany ....... 2934434

[51] Int. Cl.³ ............................................ G01N 31/08
[52] U.S. Cl. ............................................... 73/864.86
[58] Field of Search ............. 73/864.85, 864.86, 864.87

[56] References Cited

U.S. PATENT DOCUMENTS

| 3,501,176 | 3/1970 | Arms | 73/864.86 |
| 3,537,321 | 11/1970 | Barre | 73/864.86 |
| 3,566,697 | 3/1971 | Vannus | 73/864.87 |
| 3,581,573 | 6/1971 | Purcell et al. | 73/864.86 |
| 3,628,382 | 12/1971 | Vannus | 73/864.86 |
| 3,635,093 | 1/1972 | Downs et al. | 73/864.86 |
| 3,672,226 | 6/1972 | Reid | 73/864.86 |

Primary Examiner—S. Clement Swisher
Attorney, Agent, or Firm—S. A. Giarratana; F. L. Masselle; R. A. Hays

[57] ABSTRACT

A sealing apparatus useful for sealing an injection block of gas chromatograph includes means for controlling the position of a sealing body with respect to the sealing face of such an injection block.

15 Claims, 10 Drawing Figures

SEALING APPARATUS

BACKGROUND OF THE INVENTION

The present invention generally relates to a sealing apparatus for sealing the sealing face of an injection block and, in particular, relates to such apparatus having means for controlling the position of a sealing body with respect to the sealing face.

The seal of an injection block of a gas chromatograph is a critical factor in ensuring the accurate measurement of samples tested. There are two major considerations involved in attempting to properly seal such an injection block. The first major consideration is that the seal must be able to provide a quality seal even after a number of needle punctures. One problem associated with the repeated use of a particular seal beyond a relatively small number of punctures is that, during withdrawal of the needle, sample residue may remain in the sealing body and be carried into the next sample supplied and thus contaminate it. The second major consideration is that the exchanging or replacing of seals, particularly with automated sample injection apparatus, is usually a rather time consuming procedure.

One known approach to circumventing the problems discussed above is shown in U.S. Pat. No. 3,581,573 issued to Purchell et al. on June 1, 1971. The apparatus described therein comprises a sealing body having two distinct portions, a outer layer and an inner layer. Good sealing conditions are maintained by manually moving the inner layer, after it has been punctured, to present a fresh inner surface for the next puncture. While this apparatus is effective for providing a seal it nevertheless requires a two layered sealing body which is unnecessarily complicated. Another approach to the present problem is described in U.S. Pat. No. 3,646,093 issued to Downs et al. on Jan. 18, 1972. Therein a sealing member having, as an intergral part thereof a needle guide which is shifted from a seal position to a puncture position. When in the seal position the needle guide through the sealing body is covered by a solid portion of the movable member. This assembly has the drawback that the sealing body can still collect contaminents during probe withdrawal which can contaminate subsequent samples.

SUMMARY OF THE INVENTION

Accordingly it is one object of this invention to provide for a sealing apparatus which ensures excellent sealing even after a plurality of piercings.

It is a further object of this invention to employ a unitary body of self-sealing material which is cooperatively engaged to a means for controlling the position thereof with respect to the sealing face of an injection block.

These and other objects and features of the present invention will become apparent from the embodiments described in the following specification and drawing.

DETAILED DESCRIPTION OF THE INVENTION

Figure 1:
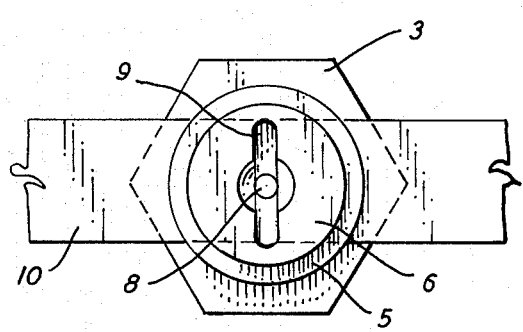
FIG. 1 is a plan view of one embodiment of the sealing apparatus, not drawn to scale, embodying the principles of the invention.
Figure 2:
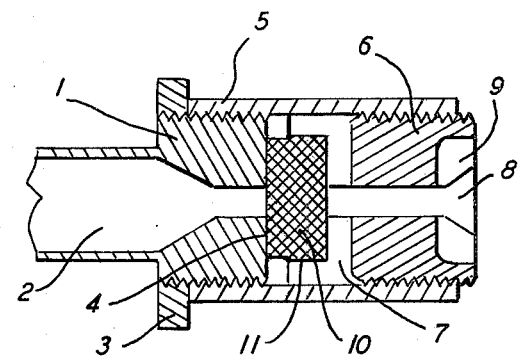
FIG. 2 is a longitudinal section through the sealing apparatus of FIG. 1 taken along the line 2—2 thereof.

Referring to FIGS. 1 and 2 an injection block, generally indicated by the reference numeral 1, of the type usually fitted into the housing of a gas chromatograph (not shown), includes an injection passage 2 which is connected to a carrier gas source in known manner and to the supply line leading to a chromatographic separating column. The injection block 1 is provided with a sealing face 4 at an external end face thereof.

The injection block 1 also includes an external thread onto which a guide sleeve 5, secured by a lock nut 3, is attached.

An urging device, described in detail hereinafter, is screwed into the guide sleeve 5 at the end thereof remote from the injection block 1. The urging device in this embodiment includes an urging member, represented by an urging screw 6, and an urging head 7 which serve to sealingly press a unitary sealing body 10 between complementarily shaped engaging faces formed at sealing face 4 and urging head 7. Urging screw 6 and urging head 7 include an internal passage 8 aligned with the injection passage 2 in injection block 1. Preferably the internal passage is flared, like a funnel, towards the exterior.

At its external face, urging screw 6 is provided with means 9, for example a slot, for engagement by a turning implement, such as a screwdriver. The rotation of urging screw 6 controls the axial position of urging head 7 within the guide sleeve 5. Thus the engagement pressure of urging head 7 on the respective sealing body 10 is adjusted by the rotation of urging screw 6. In the embodiment shown in FIGS. 1 and 2 the sealing body 10 is a flat strip of self-sealing material having a rectangular cross-section and positioned in a transverse groove 11 in the urging head 7. The body 10 presses through correspondingly shaped gaps formed on opposing sides of the guide sleeve 5, which are not shown in detail.

In operation, a test sample is introduced into the injection passage 2 by piercing the body 10 with a hollow needle inserted through internal passage 8. Prior to introducing the next sample the urging screw 6 is released and the unitary sealing body 10 is displaced in the transverse groove 11 an amount sufficient to locate an unused portion thereof between the urging head 7 and the sealing face 4. Then the urging screw 6, via a screwdriver for example, is driven into the guide sleeve 5 so as to urge the unitary sealing body 10 against the sealing face 4 with sufficient pressure to form the desired seal.

The next sample is then injected. The sealing body 10 can, if desired, be maintained in its position so long as sealing face 4 is safely sealed. However, to preclude any contamination the sealing body 10 is preferably adjusted after each sample is injected.

The shape of the sealing body 10 is not restricted to having a rectangular cross-section but can also be, for instance, an endless circular cord or tubing. However, the sealing face 4 and the urging head 7 must be complementary to the shape of the sealing body 10. Further, the gaps in guide sleeve 5 are preferably correspondingly adapted to the shape of sealing body 10. As a result, urging head 7 can then be guided non-rotatably within the guide sleeve 5.

A modified embodiment of the sealing apparatus discussed above is illustrated in FIGS. 3 and 4. For clarity, like numerals are used throughout the various Figures to designate like elements. In this instance the sealing body 10 is retained in means which form a transport carrier 30. As before, the sealing body 10 is guided within gaps formed in the guide sleeve 5. The transport carrier 30, in this embodiment, as illustrated, preferably includes a thin resilient material having a generally rectangular U-shaped pattern. The U-shaped transport carrier 30 includes shanks 31 and 32 extending toward the injection block 1. The shanks 31 and 32 are provided with teeth 33 which engage the narrow sides of the sealing body 10. Thus the body 10 is positively connected to the transport carrier 30 during movement thereof in the direction of transport. However, the sealing body 10 can freely slide in the opposite direction to the movement of transport carrier 30. The bottom portion 34 of the transport carrier 30 includes an aperture 35 through which the urging head 7 extends toward the sealing body 10. The transport carrier 30 is bent to form handles 36 at its ends. In addition, the handles 36 can also serve as points for applying fluid pressure actuated adjusting members for readjusting the sealing body 10 relative to sealing face 4, when urging screw 6 is released. If the transport carrier 30 is guided at guide sleeve 5 under low friction conditions the adjustment of the transport carrier 30 and the sealing body 10 can be accomplished even with the urging screw 6 in a tightened condition.

Figure 5:
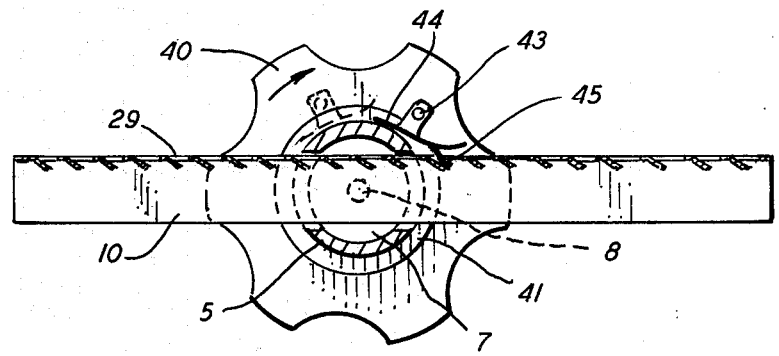
FIG. 5 is a sectional view of a sealing apparatus including adjusting means.
Figure 6:
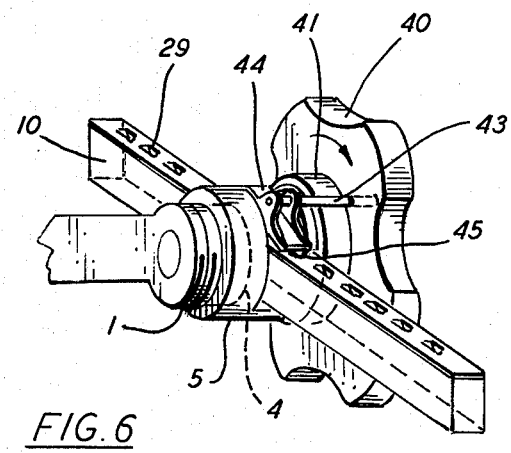
FIG. 6 is a perspective view of the sealing apparatus shown in FIG. 5.

Another embodiment of a sealing apparatus includes manually actuated adjusting means and is shown in FIGS. 5 and 6. FIG. 5 is a sectional view taken in the plane of sealing face 4, and FIG. 6 is a perspective view of this embodiment. The urging means in this embodiment comprises a handwheel 40 threaded, via an internally threaded ring 41, unto an externally threaded guide sleeve 5 at the end thereof remote from the injection block 1. The handwheel 40 includes a central pin, (not shown) which projects into guide sleeve 5 and extends into the injection passage 8 of handwheel 40. A coupling pin 43 extends from the interior face of handwheel 40 toward the injection block 1. In addition, a shoe-shaped spring catch 44 including a locking tooth 45 bent inwardly is positioned at the end of the coupling pin 43. At the top narrow side thereof the sealing body 10 is provided with a transport band 29 having a plurality of teeth which are adapted to positively interconnect the sealing body 10 to the handwheel 40 via engagement of the band 29 with the locking tooth 45.

In operation, the handwheel 40, as shown, via the locking tooth 45 of spring catch 44 is intimately engaged with the teeth in transport band 29. The central pin in the handwheel 40 urges the urging head 7 against the sealing body 10 which is thus urged against the sealing face 4. In order to readjust the sealing body 10 the handwheel 40 is rotated in the direction of the arrow by just a small amount. Then, by turning the handwheel 40 opposite to the direction of the arrow the locking tooth 45, including spring catch 44, is disengaged from the guide sleeve 5. Simultaneously the central pin 42 is displaced by a corresponding distance, which distance is dependent on the pitch of the threads in ring 41, towards the urging head 7 to thus urge the sealing body 10 against the sealing face to restore the engagement pressure required for the desired tightness. By rotating handwheel 40 again in the direction of the arrow the engagement pressure is again released and thus transport sealing body 10 another small distance by re-engaging the locking tooth 45 at another location along the transport band 29.

Alternatively, the spring catch 44 can also form a portion of a spring ring surrounding guide sleeve 5. In such an arrangement, the coupling pin at the spring catch cooperates with a cam (not shown) projecting from the interior face of the handwheel 40 to readjust the transport band 29.

The adjustment of the sealing body 10 can also be effected by pulling means acting on one end thereof. Which means can be placed under tension, to some preselected degree, such that the pulling means automatically advances the sealing body 10 upon the release of the urging head 7.

Figure 7:
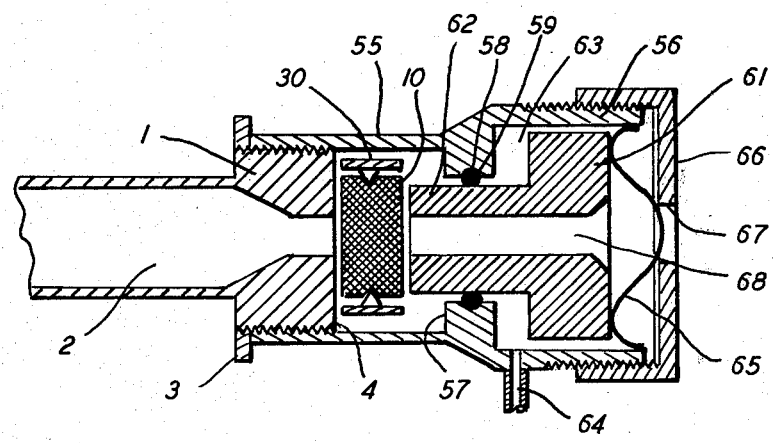
FIG. 7 is a longitudinal sectional view of still another embodiment of a sealing apparatus embodying the principles of the present invention.
Figure 8:
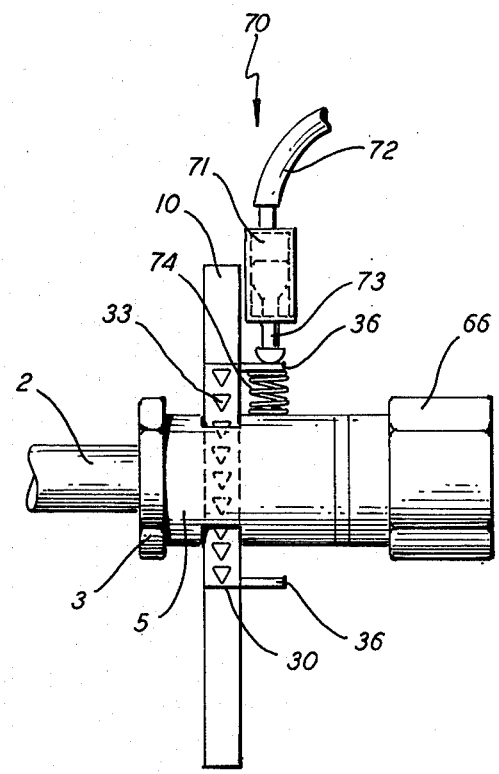
FIG. 8 is a plan view of the sealing apparatus shown in FIG. 7.

Another embodiment, particularly adapted for automatic operation is depicted in FIGS. 7 and 8.

In this embodiment, the guide sleeve 5 includes a first portion 55 which is screwed onto injection block 1 as in the embodiment shown in FIGS. 1 and 2. The guide sleeve 5 further includes an enlarged second portion 56 which is spaced apart from the first portion by an annular shoulder 57. The annular shoulder 57 has an annular groove 58 to receive a sealing ring 59. The first portion 55 of the guide sleeve 5 is provided with gaps through which the sealing body 10 extends. The urging head in the embodiment, is an urging piston the head 61 and shaft 62 of which are slideably located in the enlarged portion 56 and annular shoulder 57 of the guide sleeve 5, respectively. An annular space 63, defined by the annular shoulder 57 and by piston head 61, is provided with a connector 64 and is sealed from injection block 1 by the sealing ring 59. A spring 65 together with a knurled screw cap 66, which is preferably screwed onto an external thread of guide sleeve 5, forms an urging member for urging the piston against sealing body 10. The spring 65 preferably engages the exterior face of piston head 61. Screw cap 66 is provided with a central opening 67 which is aligned with a similar central gap in spring 65 and an interior passage 68 through the piston 61.

Figure 3:
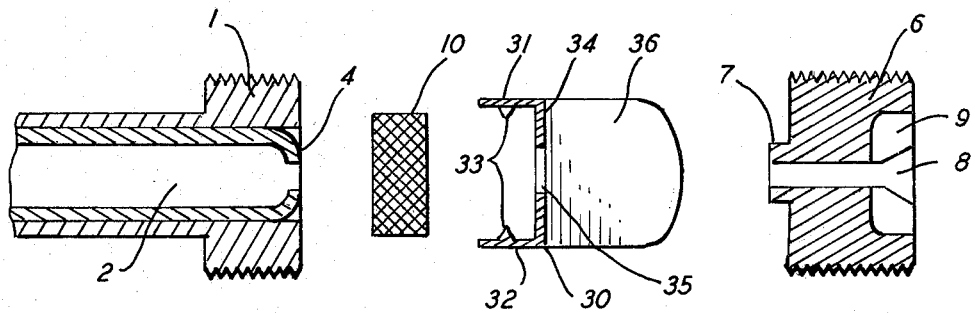
FIG. 3 is an exploded view of another embodiment of a sealing apparatus.
Figure 4:
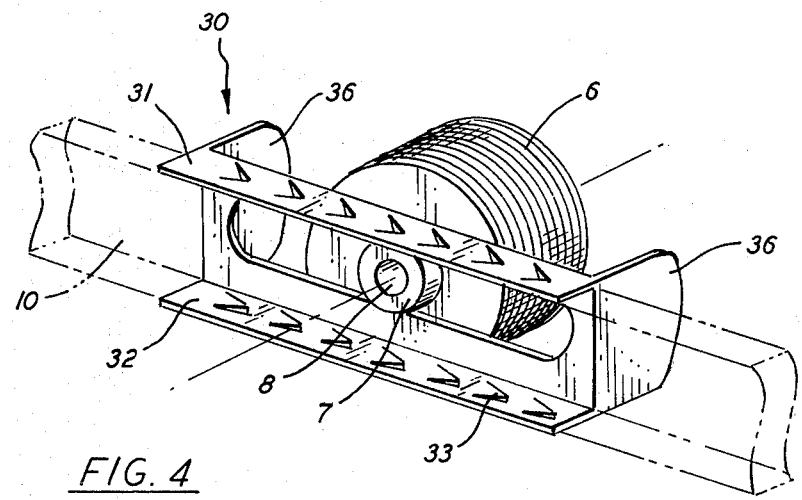
FIG. 4 is a partial perspective view of the sealing apparatus shown in FIG. 3.

The adjusting means for the sealing body 10, in this instance, comprises a serrated transport carrier 30 similar to the one depicted in FIG. 3 having a window (not shown) into which a taper, formed at the interior end of piston shaft 62, projects. The apparatus comprises pneumatic advancing means 70 which connects the connector 64 to a pressurized gas valve (not shown). The pressurized gas valve, in accordance with the cycle of operation, is synchronously controlled with an automatically operating sample feeder. The pneumatic advancing means 70 includes a pressurized gas cylinder 71 mounted, for instance, to the guide sleeve 5 fastening means, and connected to the pressurized gas valve (not shown) via supply line 72. The pressurized gas cylinder 71 contains an adjusting piston 73 the external end of which engages one of the bent angles 36, designated at 36A, of transport carrier 30. The other side of the angle 36A rests on a spring 74 externally supported at guide sleeve 5.

Upon opening the pressurized gas valve (not shown) the annular space 63 is pressurized via connector 64 and the urging piston is released from sealing body 10 against the pressure exerted by spring 65. Simultaneously, the pressurized gas cylinder 71 is pressurized and the adjusting piston 73 and therewith the transport carrier 30 including sealing body 10, is displaced against the force of spring 74. After the pressurized gas valve (not shown) is closed, the pressure in annular space 63 falls and spring 63 effects the re-engagement, under pressure, of a non-pierced location of similar body 10 against sealing face 4. The pressurized gas cylinder 71 also becomes depressurized so that the transport carrier 30, without carrying along the sealing body 10, and the adjusting piston 73 which is under the action of spring 74, return to their respective initial positions.

Generally, in an automatic sample feeder, the advance of sealing body 10 is effected by actuating members controlled by the program of the sample feeder. Thereby, in accordance with respective requirements, the advance of sealing body 10 may be initiated after injection of each sample or only after a preselected number of injections. The aforementioned means for automated, or semi-automated, operation of the sealing apparatus is only exemplary and a considerable number of other means are so commonly available that any further detailed explanation on this aspect is believed to be unwarranted.

Figure 9:
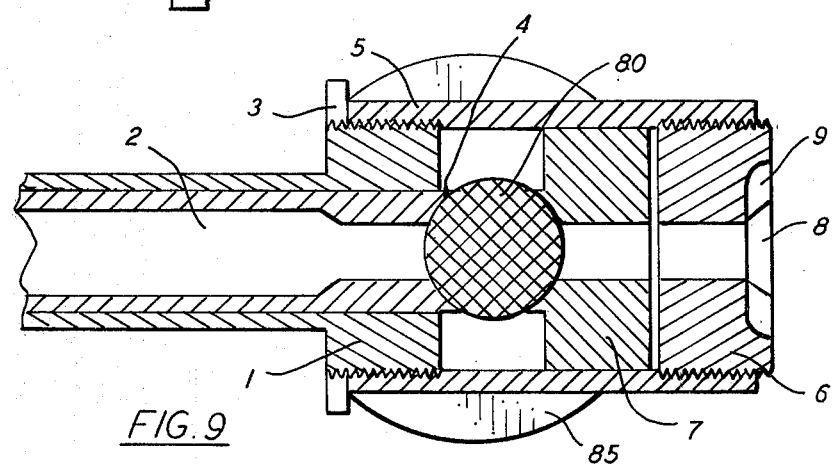
FIG. 9 is a longitudinal section view of yet another embodiment of a sealing apparatus embodying the principles of the present invention.
Figure 10:
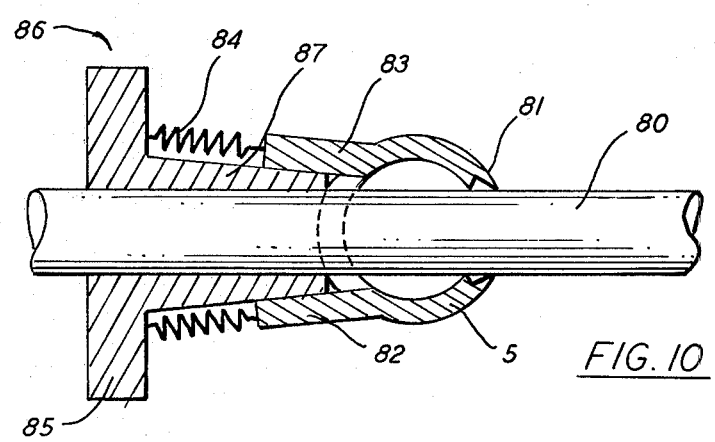
FIG. 10 is a cross-sectional view of the sealing apparatus shown in FIG. 9 taken along the line 10—10 thereof.

Yet another embodiment of a sealing apparatus is illustrated in FIGS. 9 and 10. In this embodiment, the injection block 1 includes an injection passage 2, a locking nut 3 and a cylindrical sealing face 4. A cord-like cylindrical sealing body 80 abuts the sealing face 4 under the pressure of an urging screw 6 having an urging head 7. The urging head 7 includes a correspondingly designed pressing face and is guided axially and non-interchangeably within a guide sleeve 5. The urging head 7 is preferably positioned axially and non-interchangeably in guide sleeve 5 by a tongue-and-groove guiding means, not shown in detail. In addition, the urging head 7 may be non-rotatably connected to urging screw 6. Guide sleeve 5 is provided with opposing gaps through which the cord-like cylindrical sealing body 80 extends.

The gaps for the sealing body 80 are formed differently at opposing sides of the guide sleeve 5. On one side a threaded hole 81 is formed in the wall of guide sleeve 5. The thread is designed to engage, slightly, the surface of sealing body 80 (illustrated exaggeratedly in FIG. 10). The opposing side of the sleeve is in the form of a frustro-conically guide member 82 widening outwardly and including an abutment 83. The abutment engages one end of a return spring 84 which is supported at its other end by a spring plate 85 of a clamping jaw ring 86. Preferably the spring plate 85 is knurled and the clamping jaw ring 86 can be longitudinally pushed on the sealing body 80. The clamping jaw ring 86 includes a clamping jaw 87 which is complementary with guidance gap 82.

Operationally the urging screw 6 is loosened and the clamping jaw ring 86 displaced axially along the sealing body 80. The displacement is achieved by applying pressure against the return spring 84 so that the clamping jaw 87 engages with guide member 82 at the guide sleeve 5 and is pressed against sealing body 80. Upon rotating the clamping jaw ring 86, via the spring plate 85, the sealing body 80 is also rotated. Rotation of the sealing body 80 results in its being axially displaced in the direction of the arrow. This displacement is the result of the engagement of the sealing body 10 with the thread 81. After rotation, and the resultant axial displacement, by somewhat more than the width of the piercing path, the pressure on clamping jaw ring 86 is released. The ring becomes disengaged from guide member 82 as a result of the pressure of the return spring 84 and returns to its initial position. Thus, an unpierced portion of the sealing body 80 is aligned with the internal passage 2. After rotation, the urging screw 6 is screwed into guide sleeve 5 to produce the sealing pressure desired.

In this embodiment, as shown in FIGS. 9 and 10, the sealing body 80 is arranged such that the piercing path extends diametrically thereto.

While different embodiments of the sealing apparatus embodying the principles of the present invention have been described in combination with an injection block of a gas chromatograph such an apparatus is not so limited and may be employed with other pressure-tightly sealed equipment.

What is claimed is:

1. A sealing apparatus adapted to be punctured by a needle; said apparatus comprising:
   an injection block having a passage therein adapted to receive a needle, said block having a sealing face at one end thereof;
   a unitary sealing body of self-sealing material, said body having one major surface thereof facing said sealing face of said block; said major surface being complementary to said sealing face of said block;
   a cap releasably mounted to said block at said one end thereof, said cap having an injection port therein aligned with said injection passage, said cap being adapted to accept said unitary sealing body between said injection port thereof and said injection passage of said block;
   means, integral with said cap, for urging said unitary sealing body against said sealing face whereby a pressure seal can be formed therebetween, said urging means including an urging member having an urging face adapted to abut said unitary sealing body, said urging member being cooperatively directed by a guide sleeve; said urging member being a handwheel guided on an external thread on said guide sleeve and including a central pin directed towards the interior of said guide sleeve; and
   means, cooperatively engaged with said unitary sealing body for controlling the position thereof with respect to said sealing face.

2. A sealing apparatus as claimed in claim 1, wherein said urging head is non-rotatably affixed to said guide sleeve.

3. A sealing apparatus as claimed in claim 2 wherein said urging head is axially guided in said guide sleeve in a non-interchangeable angular position relative to said guide sleeve.

4. A sealing apparatus as claimed in claim 1 wherein said sealing body forms a strip passing through gaps formed on opposing sides in said guide sleeve.

5. A sealing apparatus as claimed in claim 4 wherein said sealing body forms an endless band.

6. A sealing apparatus as claimed in claim 1 wherein said sealing body is guided in a guiding recess formed in said urging head.

7. A sealing apparatus as claimed in claim 1 wherein said sealing body is retained in adjusting means displaceable transversely with respect to said guide sleeve.

8. A sealing apparatus as claimed in claim 7 wherein said adjusting means includes a transport band engaged to one side of said sealing body.

9. A sealing apparatus as claimed in claim 7 wherein said adjusting means includes a transport carrier partially enclosing said sealing body.

10. A sealing apparatus adapted to be punctured by a needle; said apparatus comprising:
an injection block having a passage therein adapted to receive a needle, said block having a sealing face at one end thereof;
a unitary sealing body of self-sealing material, said body having one major surface thereof facing said sealing face of said block; said major surface being complementary to said sealing face of said block;
a cap releasably mounted to said block at said one end thereof, said cap having an injection port therein aligned with said injection passage, said cap being adapted to accept said unitary sealing body between said injection port thereof and said injection passage of said block; and
means, integral with said cap, for urging said unitary sealing body against said sealing face whereby a pressure seal can be formed therebetween, said urging means including an urging member having an urging face adapted to abut said unitary sealing body, said urging member being cooperatively directed by a guide sleeve; wherein said sealing body is retained by adjusting means displaceable transversely with respect to said guide sleeve; said guide sleeve including a gap having a thread for engagement with a sealing body of round cross-section and said adjusting means having a clamping jaw ring axially displaceable along said sealing body and insertable against a return spring into a conical guide formed at the opposite gap in said guide sleeve, said clamping jaw ring being rotatable therein together with said sealing body.

11. A sealing apparatus as claimed in claim 10 wherein:
said adjusting means are coupled to said urging device and are adapted to be actuated only when said urging device is released; and
a handwheel guided on an external thread on said guide sleeve acts on said adjusting means by a coupling member disposed at the interior face thereof.

12. A sealing apparatus as claimed in claim 11 wherein said adjusting means includes engaging elements for engaging complementary shaped engaging elements formed at a spring catch connected to said coupling member.

13. A sealing apparatus as claimed in claim 11 wherein said adjusting means includes angle brackets located on opposing sides of said guide sleeve one of said angle brackets being in driving connection with said coupling member, the other said angle brackets being supported at said guide sleeve by a return spring.

14. A sealing apparatus as claimed in claim 10 wherein said adjusting means includes means for pneumatically advancing said sealing body.

15. A sealing apparatus as claimed in claim 14 wherein said pneumatic advancing means includes a pressurized gas cylinder including an adjusting piston acting upon the transport carrier against a spring said advancing means being connected to a pressurized gas valve in parallel to an annular space formed between the piston head and an annular shoulder in the guide sleeve and that the urging piston is sealingly guided at said annular shoulder.

* * * * *